US008085948B2

(12) United States Patent
Thomas et al.

(10) Patent No.: US 8,085,948 B2
(45) Date of Patent: Dec. 27, 2011

(54) NOISE REDUCTION IN A SYSTEM

(75) Inventors: Fred C. Thomas, Fort Collins, CO (US); Paul Boerger, Loveland, CO (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1372 days.

(21) Appl. No.: 11/626,953

(22) Filed: Jan. 25, 2007

(65) Prior Publication Data

US 2008/0181433 A1 Jul. 31, 2008

(51) Int. Cl.

| | |
|---|---|
| ***A61F 11/06*** | (2006.01) |
| ***G10K 11/16*** | (2006.01) |
| ***H03B 29/00*** | (2006.01) |
| ***G11B 5/48*** | (2006.01) |
| ***G11B 21/16*** | (2006.01) |
| ***G06F 1/16*** | (2006.01) |
| ***G06F 12/00*** | (2006.01) |
| ***G06F 13/00*** | (2006.01) |
| ***G06F 13/28*** | (2006.01) |
| ***H05K 5/00*** | (2006.01) |
| ***H05K 7/00*** | (2006.01) |

(52) U.S. Cl. ....... 381/94.1; 381/58; 381/71.1; 381/71.7; 360/246; 360/679.33; 711/111; 711/112

(58) Field of Classification Search ................. 381/71.1, 381/71.2, 71.7, 94.1, 58; 360/246; 361/679.33–679.39; 711/157, 111, 112
See application file for complete search history.

(56) References Cited

U.S. PATENT DOCUMENTS

| | | | | |
|---|---|---|---|---|
| 5,732,143 | A | 3/1998 | Andrea et al. | |
| 6,170,037 | B1 * | 1/2001 | Blumenau | 711/114 |
| 6,470,289 | B1 | 10/2002 | Peters et al. | |
| 6,753,667 | B2 | 6/2004 | Sakamoto | |
| 7,113,605 | B2 | 9/2006 | Rui et al. | |
| 7,173,787 | B1 * | 2/2007 | Warnakulasooriya et al. | 360/69 |
| 2003/0128509 | A1 | 7/2003 | Oudet | |
| 2004/0267990 | A1 * | 12/2004 | Lin | 710/100 |
| 2005/0036286 | A1 | 2/2005 | Kuan | |
| 2005/0069144 | A1 * | 3/2005 | Delchar et al. | 381/71.3 |
| 2005/0211426 | A1 | 9/2005 | Ziarnik et al. | |
| 2005/0275365 | A1 | 12/2005 | Currie et al. | |
| 2006/0219382 | A1 | 10/2006 | Johnson et al. | |

FOREIGN PATENT DOCUMENTS

JP 17160292 6/2005

OTHER PUBLICATIONS

Jules Ryckebusch, "HeadWize," Gernsback Publications (Popular Electronics and Electronics Now), 1997, 10 pp. [Online] http://www.headwize.com/projects/noise_prj.htm.
Intel Corporation, "Serial ATA Staggered Spin-Up," Sep. 2004, Revision 1.0, A Whitepaper by: Intel Corporation, 10 pp.
International Search Report dated Jun. 11, 2008.

* cited by examiner

*Primary Examiner* — Xu Mei
*Assistant Examiner* — Douglas Suthers

(57) ABSTRACT

A system comprises a plurality of storage drives coupled to logic. The logic implements a noise-reducing feature selected from a group consisting of a first feature that limits system performance based on a level of ambient noise, a second feature that staggers access transactions among said storage drives, a third feature that staggers spin up among the storage drives, a fourth feature that at least partially cancels noise generated by the system, a fifth feature that limits fan speed, and combinations thereof.

21 Claims, 2 Drawing Sheets

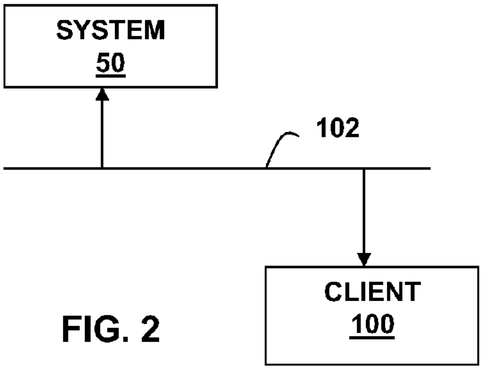
FIG. 2
58
| | |
|---|---|
| P_L1 | A_N_THRESH1 |
| P_L2 | A_N_THRESH2 |
| P_L3 | A_N_THRESH3 |
| P_L4 | A_N_THRESH4 |
FIG. 3
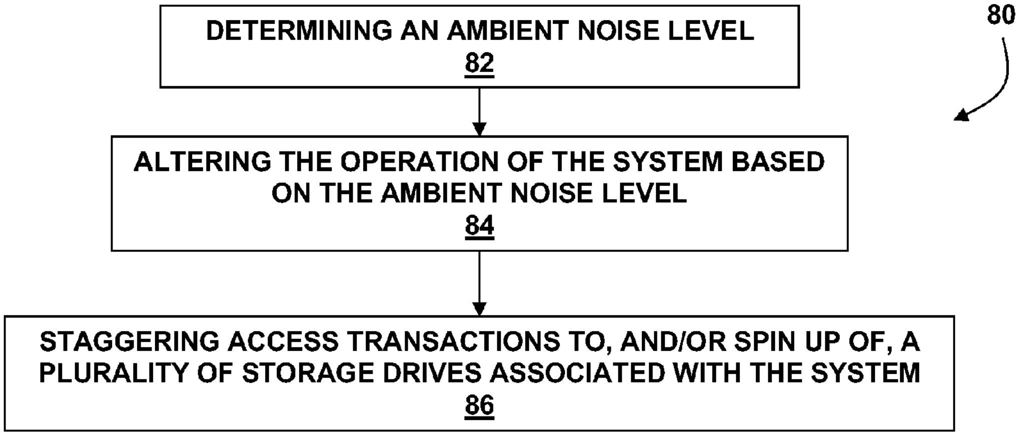
FIG. 4

NOISE REDUCTION IN A SYSTEM

BACKGROUND

Many electronic systems generate audible noise. The noise may be generated from multiple sources. For example, electronic systems generate heat and thus have a mechanism to remove the heat. That mechanism may comprise active cooling through the use of one or more noise-producing fans. Further, storage devices such as hard disk drives produce audible noise from the disk spinning and from the movement of an actuator in the drive. The actuator correctly positions the read/write head(s) in the drive.

In some situations, the audible noise generated by the system may be tolerable, while in other situations, the noise may not be tolerable. For example, a storage device on which movies are stored could be coupled to a television. A user could then select a movie for playing on the television. Such storage devices accordingly may be located in the same room (e.g., living room) as the user's television. The noise produced by the storage device's fans and disk drives may be bothersome to the user.

BRIEF DESCRIPTION OF THE DRAWINGS

For a detailed description of exemplary embodiments of the invention, reference will now be made to the accompanying drawings in which:

FIG. 2 shows a system in which a client is used to configure the system of FIG. 1 in accordance with various embodiments;

FIG. 3 illustrates a look-up table in accordance with various embodiments; and FIG. 4 shows a method in accordance with various embodiments.

NOTATION AND NOMENCLATURE

Figure 1:
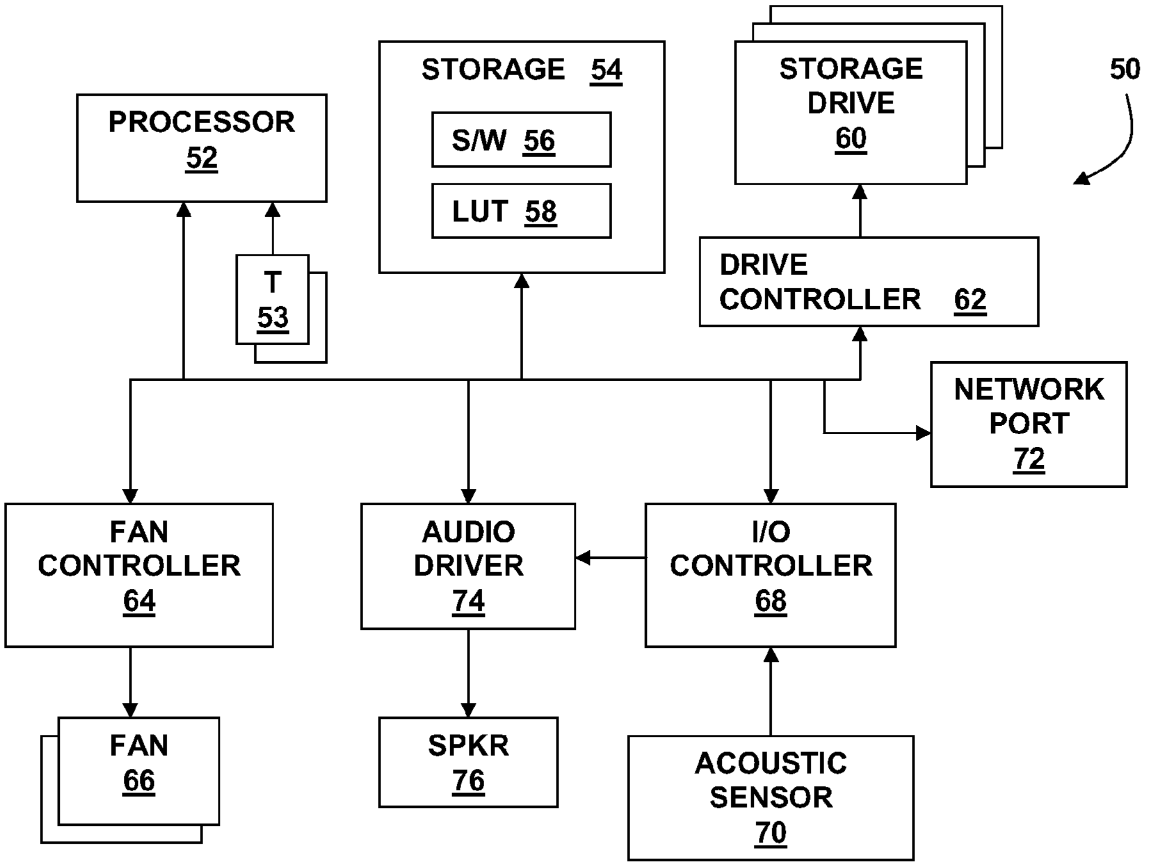
FIG. 1 shows a system in accordance with various embodiments.

Certain terms are used throughout the following description and claims to refer to particular system components. As one skilled in the art will appreciate, computer companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . . " Also, the term "couple" or "couples" is intended to mean either an indirect, direct, optical or wireless electrical connection. Thus, if a first device couples to a second device, that connection may be through a direct electrical connection, through an indirect electrical connection via other devices and connections, through an optical electrical connection, or through a wireless electrical connection.

DETAILED DESCRIPTION

FIG. 1 shows an embodiment of a system 50 comprising a processor 52, one or more temperature sensors 53, storage 54, one or more storage drives 60, drive controller 62, fan controller 64, one or more fans 66, an input/output controller 68, an acoustic sensor 70 (e.g., microphone), a network port 72, an audio driver 74, and one or more speakers 76. In some embodiments, more than one acoustic sensor 70 is provided. The storage 54 comprises volatile memory (e.g., random access memory), non-volatile memory (e.g., Flash memory, read only memory, etc.) and combinations thereof. The processor 52 executes software 56 stored on the storage 54. The processor 52, executing the software 56, causes the system 50 to provide some or all of the functionality described herein.

Each storage drive 60 comprises any suitable type of mass storage device. Examples include hard disk drives and compact disk read only memory (CDROM) drives. In some embodiments, system 50 comprises a storage system in which one or more users/clients can store various types of data. For example, the system 50 can be used to store movies or other types of video or audio for playback on a television.

The processor 52, storage drives 60 and other components in system 50 generate heat during normal operation and thus fans 55 are provided to remove the heat generated by the system 50. The fan controller 64 is controlled by the processor 52 and provides control signals to the fans 66 to enable and disable the fans as well as to control the speed at which each fan spins. As the amount of heat generated by the system increases, the fan controller 64 may cause one or more of the fans to spin at a faster rate. The temperature sensors 53 are used to measure the heat generated by the system 50.

In some embodiments, the acoustic sensor 70 is used to detect ambient noise in the environment in which the system 50 is located. The acoustic sensor 70 may be hard-wired or wirelessly coupled to the I/O controller 66. The acoustic sensor 70 detects ambient noise and provides a value indicative of the ambient noise level to the processor 52 via the I/O controller 68.

System 50 generates audible noise from at least two sources in the embodiment of FIG. 1. One source is the fans 66. The spinning of a fan 66 generates noise and the magnitude of the noise level produced by a fan is a function of the speed at which the fan spins. The faster a fan spins, the more noise it generates.

Another source of noise is the storage drives 60. A storage drive 60 comprises a magnetic disk (in the case of a hard disk drive) that spins thereby producing noise. Further, each storage drive 60 comprises an actuator that moves a read/write head to an appropriate location on the spinning disk. The movement of the actuator also produces noise.

In accordance with various embodiments, system 50 operates in one of multiple selectable modes of operation. In some embodiments, the system 50 has few, or no, user controls. In such embodiments, a separate device is used to select the mode of operation for the system 50. FIG. 2 illustrates the use of a separate client device 100 that couples to the system 50 via a network 102. The system's network port 72 (FIG. 1) enables the system 50 to be coupled to the network 102 to which the client device 100 also couples. The network 102 may comprise a wired-network (e.g., Ethernet) or a wireless network.

The client 100 comprises a personal computer (PC) in some embodiments. Via the client 100, a user selects an operational mode for, and/or otherwise configures, the system 50. One such operational mode comprises a "quiet" mode and another operational mode comprises a "performance" mode. In the performance mode, the system 50 is configured to achieve the highest performance possible without regard to the noise generated by the fans 66 and the storage drives 60. For example, in the performance mode, the processor 52 is clocked at a higher speed than in the quiet mode. As such, in the performance mode the processor 52 consumes more power and produces more heat than in the quiet mode. The processor 52 receives temperature readings from the temperature sensor(s) 53 and causes the fan controller 64 to both enable the fans 66 and increase the speed of the fans as necessary to adequately cool the system without regard to the resulting noise created by the fans 66. Further, in the performance mode, the processor 52 accesses the storage drives 60 as needed to perform read and write access transactions without regard to the noise produced by the drives.

In the quiet mode, however, one or more features are implemented to cause the system 50 to produce less noise than otherwise would be the case in the performance mode. For example, such features comprise:

(1) limiting performance of system 50 based on a level of ambient noise (e.g., powering down one or more heat producing subsystems within system 50),
(2) staggering access transactions among the storage drives 60,
(3) staggering spin up among the storage drives 60,
(4) at least partially canceling noise generated by the system 50, and
(5) limiting the speed of one or more of the fans 66.

In various embodiments, any of the aforementioned noise-reducing features are implemented in the quiet mode. Further, any combination of two or more of noise-reducing features are implementable in the system's quiet mode. Each of the four noise-reducing features is now described.

The first feature comprises limiting the performance of the system 50 based on the magnitude of ambient noise in the area of the system 50. For example, if the room in which the system 50 is located is noisy, then the performance level of the system 50 can be increased (relative to a room that is less noisy). A higher performance level (e.g., processor being clocked at faster rate) generally will result in increased heat being generated by the system 50 which, in turn, will result in the fan controller 64 causing the fans 66 to spin at a faster rate to adequately cool the system. Since, in this example, the room in which the system 50 is located, is noisy, system 50, to a certain extent, can generate more noise without being bothersome to the people in the room.

As shown in FIG. 1, a acoustic sensor 70 is provided for system 50. In some embodiments, the acoustic sensor 70 is mounted on a chassis in which the components of the system 50 are provided. In other embodiments, the microphone is located remote from the system's chassis and coupled to the system via a wire or a wireless connection. For example, the acoustic sensor 70 could be located at or near the location at which a user would located typically be when using the system 50 (e.g., while watching a movie streamed from the system 50 to a television). Thus, the acoustic sensor 70 is used to control the performance level of the system 50 based on ambient noise detected at the user's location, which may or may not be immediately adjacent the system 50.

The acoustic sensor 70 thus detects ambient noise and provides an ambient noise level value to the processor 52 which adjusts the system performance based on the ambient noise level value. The adjustment to the system's performance comprises, for example, throttling the processor's clock frequency. The clock frequency is adjusted up or down depending on the ambient noise level as detected via acoustic sensor 70. The clock frequency can be adjusted to a relatively high level in the face of high ambient noise or adjusted to a relatively low level in the face of low ambient noise.

In accordance with at least some embodiments, the processor 52 uses the ambient noise level value generated by the acoustic sensor 70 as an index into a look-up table (LUT) 58 stored in storage 54. As illustrated in FIG. 3, the LUT 58 contains a plurality of target performance levels (P_L1, P_L2, etc.) corresponding to various ambient noise level thresholds (A_N_THRESH1, A_N_THRESH2, etc.). For example, each target performance level contained in LUT 58 corresponds to an ambient noise level threshold. As shown in FIG. 3, for example, the performance level designated as P_L1 corresponds to the ambient noise threshold designated as A_N_THRESH1. Although four sets of performance levels/ambient nose thresholds are shown in FIG. 3, any number of such sets is possible. In accordance with various embodiments, the LUT 58 is configured during manufacturing of the system 50. In various embodiments, the performance levels assigned to the various ambient noise levels is such that the system 50 will generate maximum noise at a level not greater than a predetermined threshold noise margin (e.g., 30 dBA) below the level of ambient noise. Prior testing of the system 50 can be performed to determine the noise levels generated by the system at each of the various performance levels. The processor 52 thus retrieves from the LUT 58 a target performance level for the detected ambient noise level and configures the system 50 for that target performance level.

Another noise-reducing feature is to stagger access transactions (reads and writes) among the storage drives 60, assuming the system 50 has more than one storage drive 60. In some situations, the processor 52 may have read or write transactions to be performed to multiple storage drives 60 and, for performance reasons, can have such transactions performed simultaneously to the multiple storage drives. A storage drive's actuator generates noise as a transaction is processed by that drive. With multiple storage drives simultaneously performing access transactions, the noise level from the storage drives as a group is greater than the noise generated by a single drive's actuator.

In accordance with various embodiments, however, the drive controller 62 staggers access transactions among the various storage drives 60. For example, if a read or write access transaction is pending for each of the storage drives 60, the drive controller 62 causes one access transaction at time to be performed by a particular drive. The total elapsed time to perform all of the pending access transactions is longer than if the transactions were permitted to be performed simultaneously by the storage drives 60, but the resulting noise level will be less bothersome to a user because the actuators of the storage drives are not all being activated simultaneously.

In some such embodiments, the drive controller 62 enables access transactions to be performed simultaneously by multiple, but not all, storage drives 60. The number of drives 60 permitted to perform simultaneous transaction accesses is based, in some embodiments, on the ambient noise level as detected by acoustic sensor 70. In a relatively noisy environment, the drive controller 62 may permit access transactions to be performed to, for example, two storage drives simultaneously, while other pending access transactions targeting another drive(s) are forced to wait.

A drive 60 may be spun down, for example, on powering down the system 50 or after a period of inactivity. When that drive is again needed (e.g., for a read or write access transaction), the storage medium of the drive must be spun up to an operational speed. Often, a drive is noisier when during its spin-up phase than after it reaches a steady state speed. Accordingly, in accordance with the third noise-reducing feature listed above, the drive controller 62 staggers spin up of the various storage drives 60. For example, if multiple drives need to be activated, the drive controller 62 causes each drive to begin spinning up in a staggered fashion. One drive's spin-up phase can be overlapped with the spin-up phase of another drive. For example, a first drive begins to be spun up. After that drive has started spinning up, but before its steady state speed has been reached, a second drive begins to spin up. The first drive reaches its steady state speed before the second drive reaches its own steady state speed. In other embodiments, the spin-up phases of the drives do not overlap and, instead, are performed sequentially. The total elapsed time to spin up all drives 60 is longer than if the drives were spun up simultaneously, but the resulting noise level will be less bothersome to a user.

In some such embodiments, the drive controller 62 enables multiple, but not all, storage drives 60 to be spun up simultaneously. The number of drives 60 permitted to be spun up simultaneously is based, in some embodiments, on the ambient noise level as detected by acoustic sensor 70. In a relatively noisy environment, the drive controller 62 may permit, for example, two storage drives to be spun up simultaneously, while another drive begins its spin-up phase at a later point in time.

The fourth listed noise-reducing feature comprise noise cancellation. In such embodiments, more than one acoustic sensor 70 and more than one speaker 76 are used. In at least some embodiments, the ambient noise waveform, generated by the acoustic sensors 70, is provided via the I/O controller 68 to the audio driver 74 (FIG. 1). The audio driver 74 implements noise cancellation by, for example, computing a signal that corresponds to the input ambient noise waveform, but is substantially 180 degrees out of phase with respect to the input ambient noise waveform. The out of phase signal is then provided to the speaker 76 which generates an out of phase audio signal. The out of phase audio signal produced by the speaker 76 substantially cancels the noise generated by the system 50 itself.

Using noise cancellation, in some embodiments the system 50 can be permitted to operate at a high performance level while ameliorating the bothersome effects of the noise being generated by the system. In other embodiments, noise cancellation is implemented in conjunction with one or more of the other noise-reducing features described herein.

FIG. 4 illustrates a method 80 comprising actions 82-86 which are useful to reduce the noise generated by the system 50. At 82, method 80 comprises determining an ambient noise level. At 84, the method comprises altering the operation of the system 50 based on the determined ambient noise level. Five examples of such alterations are listed above (limiting performance, staggering access transactions, staggering spin up, noise cancellation, and fan speed limiting). At 86, the method further comprises staggering access transactions to, and/or or spin up of, the storage drives 60. These actions 82-84 can be performed in any order and other noise-reducing techniques can be employed as well. Further, method 80 may include noise-reducing techniques different from those shown in FIG. 4.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A system, comprising:
- a plurality of storage drives; and
- logic coupled to said storage drives, said logic implements at least one noise-reducing feature comprising time staggering access transactions among at least two of said storage drives based on an ambient noise level.

2. The system of claim 1 further comprising an acoustic sensor coupled to said logic, said acoustic sensor detects ambient noise and provides an ambient noise level value to said logic which adjusts a system performance based on said ambient noise level value.

3. The system of claim 2 wherein said logic limits the system performance to a level which causes the system to generate noise at a level not greater than a predetermined threshold noise margin below said level of ambient noise.

4. The system of claim 1 wherein said access transactions comprise read and write transactions.

5. The system of claim 1 wherein said logic implements another noise-reducing feature comprising staggering spin up of said storage drives.

6. The system of claim 1 further comprising an acoustic sensor coupled to said logic, wherein said logic generates a sound signal that is substantially out of phase with respect to a sound signal detected by said acoustic sensor.

7. The system of claim 6 further comprising a speaker coupled to said logic, said logic provides said substantially out of phase sound signal to said speaker.

8. The system of claim 1 further comprising an acoustic sensor wirelessly coupled to said logic, said wireless acoustic sensor providing a signal indicative of the level of ambient noise to said logic.

9. The system of claim 1 further comprising an acoustic sensor that provides a signal indicative of the ambient noise level to the logic.

10. The system of claim 1 wherein the logic selects a number of storage drives whose access transactions occur simultaneously, said number being dependent on a signal indicative of the ambient noise level, and access transactions to all other storage drives being time staggered.

11. A system, comprising:
- a plurality of storage drives; and
- logic coupled to said storage drives, said logic implements multiple operational modes comprising at least a first mode in which noise generated by the system is ameliorated by time staggering access transactions among at least two of said storage drives based on an ambient noise level.

12. The system of claim 11 in which the operational modes also comprise a second mode in which system performance is higher than in said first mode.

13. The system of claim 11 wherein said logic receives configuration input from a computer external to said system, said configuration input causing the system to operate in at least one of the multiple modes.

14. The system of claim 11 further comprising an acoustic sensor coupled to said logic, said acoustic sensor detects ambient noise and provides an ambient noise level value to said logic which adjusts system performance based on said ambient noise level value.

15. The system of claim 11 further comprising an acoustic sensor coupled to said logic, said acoustic sensor detects ambient noise and provides an ambient noise level value to said logic which time staggers access transactions among said storage drives by enabling access transactions to be performed simultaneously to as many drives as possible so that the noise generated by the system is less than a predetermined threshold noise margin below said level of ambient noise while precluding access transactions from being performed to at least one other storage drive.

16. The system of claim 11 further comprising an acoustic sensor coupled to said logic, said acoustic sensor detects ambient noise and provides an ambient noise level value to said logic which staggers spin up among the storage drives by enabling as many drives as possible to be spun up simultaneously so that the noise generated by the system is less than a predetermined threshold noise margin below said level of ambient noise while precluding at least one other storage drive from being spun up.

17. The system of claim 11 further comprising an acoustic sensor coupled to said logic, wherein said logic generates a sound signal that is substantially out of phase with respect to a sound signal detected by said acoustic sensor.

18. The system of claim 11 further comprising an acoustic sensor wirelessly coupled to said logic, said wireless acoustic sensor providing a signal indicative of the level of ambient noise to said logic.

19. The system of claim 11 further comprising an acoustic sensor that provides a signal indicative of the ambient noise level to the logic.

20. A method, comprising:

determining an ambient noise level; and time staggering access transactions among a plurality of storage drives based on the ambient noise level.

21. The method of claim 20 further comprising staggering spin up of the plurality of storage drives associated with said system.

* * * * *